United States Patent [19]

Anraku

[11] Patent Number: 5,041,558

[45] Date of Patent: Aug. 20, 1991

[54] ACCELERATOR OF THE ACTIVITY OF HYDROLASE

[75] Inventor: Hideo Anraku, Ibaraki, Japan

[73] Assignee: Sekisui Kagaku Kogyo Kabushiki Kaisha, Osaka, Japan

[21] Appl. No.: 36,886

[22] Filed: Apr. 10, 1987

[30] Foreign Application Priority Data

Apr. 11, 1986 [JP] Japan .................................. 61-84455
Apr. 11, 1986 [JP] Japan .................................. 61-84456
Apr. 11, 1986 [JP] Japan .................................. 61-84457
Sep. 29, 1986 [JP] Japan ................................ 61-230478

[51] Int. Cl.$^5$ ................ C07D 493/00; C07D 309/10; C07D 325/00
[52] U.S. Cl. ................................. 549/210; 549/277; 549/384; 514/802
[58] Field of Search ............... 549/390, 384, 383, 210, 549/276, 277, 278; 548/403; 514/492, 502, 802

[56] References Cited

U.S. PATENT DOCUMENTS 3,093,659  6/1963  Bell et al. ............................ 549/206
3,177,237  4/1965  Muetterties ......................... 556/13
3,647,842  10/1974  Wilkes .................................. 556/41

FOREIGN PATENT DOCUMENTS

A0159917  3/1989  European Pat. Off. .
6011519   6/1983  Japan .
6027858   7/1983  Japan .
60174952  2/1984  Japan .

OTHER PUBLICATIONS

Bock et al., Biochemistry, vol. 20, pp. 7258-7266, 1981.
Anraku, Chemical Abstracts, vol. 104, 1986.
Chemical Abstracts, vol. 104, No. 5, Feb. 3, 1986, p. 298, abstract no. 31394b, Columbus, Ohio, U.S., & JP-A-60 174 952, 09-09-85 *Abstract*.
Patent Abstracts of Japan, vol. 10, No. 41 (P-429) [2098] Feb. 18, 1986; & JP-A-60 186 760, 24-09-1985, *Abstract*.
Chemical Abstracts, vol. 102, No. 25, Jun. 24, 1985, p. 324, abstract no. 217869z, Columbus, Ohio, U.S.; & JP-A-60 27 858, 12-02-1985 *Abstract*.
Chemical Abstracts, vol. 97, 1982, p. 770, abstract no. 128074x, Columbus, Ohio, U.S.; & US-A-4 329 798 (Allied Corp.) 11-05-1982, *Abstract*.
Chemical Abstracts, vol. 98, 1983, p. 644, abstract no. 53598f, Columbus, Ohio, U.S.; A. Inada et al.
Chemical Abstracts, vol. 76, 1972, p. 508, abstract no. 127110k, Columbus, Ohio, U.S.; F. F. Farris et al.
Journal of the American Chemical Society, vol. 104, No. 6, Mar. 24, 1982, pp. 1555-1560, C. C. Felix et al.
Chemical Abstracts, vol. 92, 1980, p. 691, abstract no. 58948f, Columbus, Ohio, U.S., D. A. Clarke et al.
Chemical Abstracts, vol. 91, 1979, p. 620, abstract no. 123856v, Columbus, Ohio, M. M. Hunt et al.

Primary Examiner—Jose G. Dees
Assistant Examiner—Deborah D. Carr
Attorney, Agent, or Firm—Irell & Manella

[57] ABSTRACT

An accelerator of the activity of hydrolase consisting of a coordination compound or a metal complex containing, as a ligand, an organic cyclic compound with carbonyl groups adjacent to each other in the structure shown in the following general formula I that are substantially in the same plane as each other;

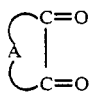

(I)

(wherein A is the cyclic compound moiety.)

6 Claims, No Drawings

ACCELERATOR OF THE ACTIVITY OF HYDROLASE

BACKGROUND OF THE INVENTION

1. Field of the Invention:

This invention relates to an accelerator of the activity of hydrolase, especially one that accelerates the activation of the precursors of serine protease, including blood coagulation Factor XII, and that accelerates the enzyme activity of serine protease produced by the activation of the said precursors. Moreover, this invention relates to an accelerator of blood coagulation with the use of the said accelerator.

2. Description of the Prior Art:

The remarkable progress in testing techniques coupled with the spreading of blood tests including serum biochemistry tests, serum immunology tests, and blood cell tests is contributing much to the prevention of disease and to early diagnosis. Most blood tests are tests of the serum, and the serum that is needed for such tests is, as a rule, obtained by blood that is collected into a container for blood tests and allowed to coagulate, after which centrifugation takes place, by which the blood clot (the gel-like mass of a mixture of fibrin and blood cells), which has a different specific gravity from that of the serum, is separated therefrom, and the serum is collected with the use of a pipette or by decantation.

A relatively long period of time is needed for blood collected from subjects to be tested to coagulate. For example, even if glass test vessels, which allow blood to coagulate in a relatively short period of time, are used, it takes 40-60 minutes until coagulation, and if test vessels made of a synthetic resin are used, the vessels must be left for 4 hours or more. For that reason, there is the problem that it is not possible to obtain serum needed for tests speedily. This is a particular problem when the test is to be done in a emergency.

A blood coagulation accelerator is used so that blood will coagulate rapidly. Factor XII is one form of precursor of a protein hydrolase (serine protease) related to blood coagulation, and by its activation, other blood coagulation factors in the blood are activated in turn to start blood coagulation. As accelerators of the activity of Factor XII, conventionally, glass, kaolin, bentonite, silica, and other inorganic fine or coloidal particles, and ellagic acid are known. These are also used as one ingredient among the reagents for the measurement of the activated partial thromboplastin time (APTT), which is one kind of test of coagulation functioning. However, even if these are used as blood-coagulation accelerators, differences in their purity and composition cause scattering of the results for tests such as the time for blood coagulation. In addition, even if these accelerators of blood coagulation are used to promote coagulation of the blood, the separation effect of the blood serum and the blood clot is incomplete, so when centrifugation is done to obtain the serum, some components of the blood clot are mixed into the serum, which is a disadvantage.

A further problem arises when serum is obtained from the blood of patients who receive hemodialysis or patients with blood-clotting disorders. Such patients are given heparin to prevent the formation of clots, so 1-20 units of heparin is found in every 10 ml of their blood. This heparin binds with antithrombin III in their blood and strongly inhibits the effects of thrombin. It is said that the heparin also inhibits the effects of blood coagulation factors including Factor XII. For that reason, fibrinogen does not become fibrin, and so blood does not coagulate. Even if the accelerators of blood coagulation mentioned above are added, the blood does not actually coagulate, and so it is difficult to obtain the serum.

The inventors of this invention have proposed in Japanese Laid Open Patent Publication No. 60-115519 that an organic cyclic compound with the following general formula has carbonyl groups adjacent to each other in the structure that are substantially in the same plane as each other and is useful for accelerators of the activity of hydrolase, which can be used for accelerators of blood coagulation.

(wherein A is the cyclic compound moiety.)

As above mentioned compounds, for example, there are oxidized alkyl gallate, oxidized ellagic acid, etc. These compounds non-enzymatically activate blood coagulation Factor XII, and make it possible for the blood to coagulate in a relatively short period of time. The effect is stronger than that obtained with the use of conventional accelerators of blood coagulation. The inventors have also proposed an accelerator of blood coagulation in which these compounds are the main ingredient, or in which various additives are added to these compounds. For example, applications have already been filed for an accelerator of blood coagulation that contains protein hydrolase as a co-accelerator to promote further the coagulation of the blood (Japanese Laid Open Patent Publication No. 60-174952) and for an accelerator of blood coagulation that includes a neutralizer of heparin so that the heparin in the blood of patients receiving heparin will be neutralized (Japanese Laid Open Patent Publication No. 60-27858).

It is possible to use all kinds of proteases including trypsin, thrombin, and cathepsin B as protein hydrolases for the acceleration of blood coagulation. These protein hydrolases act to accelerate the activation of blood coagulation factors in the blood, so the blood coagulates rapidly. For the neutralizer of heparin mentioned above, compounds with amine salts and/or a quaternary nitrogen can be used, including alkylamine hydrochloride. With an accelerator of blood coagulation that includes such compounds, the above-mentioned amine salts, etc., adsorb onto heparin, neutralizing it, and act to inactivate the heparin; moreover, the compounds with the structure of formula I activate blood coagulation Factor XII in the blood, so that it becomes possible for the blood to coagulate in a short period of time.

As mentioned above, by the use of an accelerator of blood coagulation containing compounds of the structure shown in formula I as the main ingredient, it is now possible to obtain serum from blood that has coagulated in a short period of time, having been taken from either healthy persons or patients given heparin. There is not a large scattering in the time taken for the blood to coagulate. However, the compounds of the structure shown in formula I mutually interact with some components of blood and influence the data obtained by clinical examinations, so that the use of the compounds as the main ingredient of an accelerator of blood coagulation must be limited.

SUMMARY OF THE INVENTION

The accelerator of the activity of hydrolase of this invention, which overcomes the above-discussed and numerous other disadvantages and deficiencies of the prior art, consists of a coordination compound, namely a metal complex containing, as a ligand, an organic cyclic compound with carbonyl groups adjacent to each other in the structure shown in the following general formula I that are substantially in the same plane as each other;

 (I)

(wherein A is the cyclic compound moiety.)

In a preferred embodiment, the hydrolase is serine protease.

In a preferred embodiment, the hydrolase is blood coagulation Factor XII.

The accelerator of blood coagulation of this invention contains the above-mentioned accelerator of the hydrolase activity.

In a preferred embodiment, the accelerator of blood coagulation further contains hydrolase as a co-accelerator, the hydrolase being an enzyme that can hydrolyze the bond between Arg and any amino acid residue and/or the bond between Lys and any amino acid residue on a peptide chain.

In a preferred embodiment, the hydrolase contained in the said acceleration of blood coagulation is at least one selected from serine protease, thiol protease, and metal protease.

In a preferred embodiment, the accelerator of blood coagulation further includes an organic compound that has an amino salt and/or a quaternary nitrogen.

In a preferred embodiment, the accelerator of blood coagulation further includes an anti-fibrinolysis agent and/or an anti-plasmin agent.

For these reasons, the invention disclosed herein makes possible the objects of (1) providing an accelerator of the activity of hydrolase that can be an excellent accelerator of blood coagulation; (2) providing an accelerator of the activity of hydrolase as mentioned above that is readily manufactured and refined; (3) providing an accelerator of the activity of hydrolase that can be stored for long periods of time because it is relatively stable against heat; (4) providing an accelerator of blood coagulation that includes the accelerator of the hydrolase activity and promotes the coagulation of blood in a short period of time; (5) providing an accelerator of blood coagulation that gives good separation effect of the serum and the blood clot and separates the serum from the blood clot in a high yield; (6) providing an accelerator of blood coagulation that does not change the serum, so the serum can be used for every kind of biochemical test and clinical test to give accurate results at all times with reliability; (7) providing an accelerator of blood coagulation that promotes the speedy coagulation of blood even if the blood contains heparin, and with which there is stability even after coagulation, and also good separation of serum.

DESCRIPTION OF THE PREFERRED EMBODIMENTS

The compounds shown in formula I below, which are a ligand of the coordinate compound, namely a metal complex (i.e., the accelerator of the activity of hydrolase of this invention), can be homocyclic compounds or heterocyclic compounds; also, they can be monocyclic or polycyclic compounds.

 (I)

(wherein A is the cyclic compound moiety.)

As these cyclic compounds, a six-membered ring or a five-membered ring that contains the two carbonyl groups shown in formula I is preferable.

Of the homocyclic compounds, the preferred six-membered ring is a compound with an o-quinone shown below in general formula II:

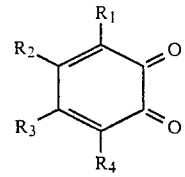 (II)

(wherein $R_1$, $R_2$, $R_3$ and $R_4$ are hydrogen, hydrocarbon, polar group or polycyclic compound moiety, independently.)

Formula II is not limited to hydrocarbons; alkyl groups, and particularly alkyl groups with 1 to 18 carbon atoms, are preferred. Examples of the polar substitution group are carboxyl groups, carboxylic acid esters, hydroxyl groups, amino acids, mercapt groups, etc., but they are not limited thereto. As the compound that has an o-quinone ring, o-quinone and other compounds shown below in formulae III-VII can be mentioned:

Oxidized alkyl gallate

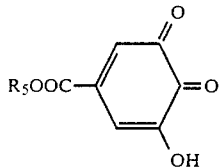 (III)

(wherein $R_5$ is alkyl.)

Partially oxidized ellagic acid

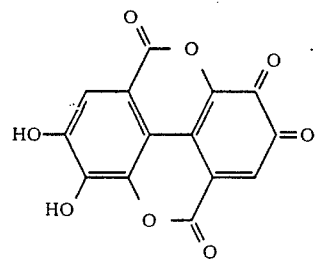 (IV)

Completely oxidized ellagic acid

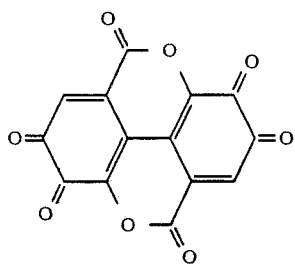

Partially oxidized 1,4-di(3,4-dihydroxyphenyl)2,3-dimethylbutane

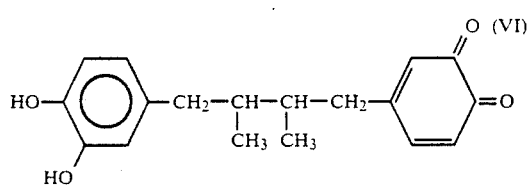

Completely oxidized 1,4-di(3,4-dihydroxyphenyl)2,3-dimethylbutane

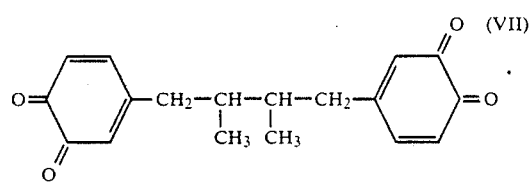

As a preferred example of the five membered ring compounds which belong to the homocyclic compounds, there is 1,2,3-triketohydroindene shown below in formula VIII.

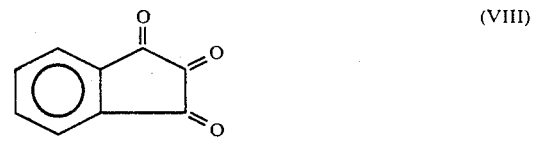

As heterocyclic compounds, there are, e.g., compounds (IX) shown below.

(wherein $R_6$ is hydrogen or hydrocarbon, polycyclic compound moiety; and $R_7$ and $R_8$ is hydrogen, polar group or polycyclic compound moiety, independently. The hydrocarbon and polar group are as defined in formula II.)

As a preferred example of the compounds shown in formula (IX), there is, e.g., isatin shown below.

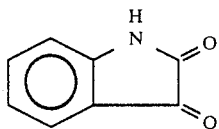

The metals that form the complex are metals other than alkaline metals that have o,o-ligands. The handling of complexes containing Fe, Co, Ni, Al, etc., is particularly facile, so they are preferred. The metal complex that is the accelerator of the activity of hydrolase of this invention can be obtained by the addition of a salt solution that contains the above-mentioned metal ions to a compound I that becomes the above-mentioned ligand. For example, by the addition of an aqueous solution of hydrochloride, sulfate, etc., alone or by the addition of a mixture of these aqueous solutions, it is possible to obtain the metal complex as a reaction product. This reaction product is recovered as a precipitate when the pH of the solution is adjusted appropriately, and it is also possible to use the reaction product in the form of a solution. For example, an oxidized propyl gallate-iron complex can be obtained from a mixture of a solution containing oxidized propyl gallate with a solution of ferric chloride. In such a metal complex, there can be a ligand that contains one or more kinds of halogen radicals, sulfuric acid moiety, nitric acid moiety, and ammonium moiety. Water can be also included as a ligand.

The accelerator of blood coagulation of this invention may be further comprised of hydrolase as a co-accelerator. The accelerator of the present invention increases the activity of hydrolase and may be used in combination with a hydrolase co-accelerator. This hydrolase is a protease that can hydrolyze the bond between Arg and any amino acid residue or the bond between Lys and any amino acid residue on the peptide chain. As such a protease, there are, for example, serine proteases such as trypsin, thrombin, snake venom thrombin-like enzymes, etc.; thiol proteases such as cathepsin B and ficin, etc.; and metal proteases such as kinase I, etc. In particular, serine proteases are suitable for use. These proteases used alone act to accelerate blood coagulation, and when used together as a co-accelerator with the accelerator (metal complex) of the activity of hydrolase mentioned above, the activation of blood coagulation is even more rapid.

When the hydrolase mentioned above is included, then it is included in the proportion of $10^{-2}-10^7$ parts by weight of the said enzyme ($10^1-10^{10}$ units) for every 100 parts by weight of the metal complex. Even if there is too little enzyme included, blood coagulation will be accelerated if there is the metal complex present, but compared to the case when the enzyme is provided in the proportions mentioned above, the effects are much smaller; if there is an excess, the effects compared with those obtained with the proportions mentioned above are not achieved.

Also, in the accelerator of blood coagulation of this invention, an organic compound that includes amines salts and/or a quaternary nitrogen can be present. These compounds adsorb onto heparin, neutralizing it, and are used as agents to neutralize heparin. As amines constituting the amine salts, primary, secondary, and tertiary amines are all acceptable, and the acid in the structure of the amine salt can be either an inorganic acid or an organic acid. As an inorganic acid, halohydro-acids, sulfuric acid, sulfurous acid, etc., can be used, and as an organic acid, there are formic acid, acetic acid, etc. Usually, the organic residue of an amine salt is an alkyl group, but it can also be a hydrocarbon group including a different element such as an imino group, ether group, or so on. The amine salt can also be an intramolecular salt.

As a preferred example of the amine salts, for example, these are hexadecyldimethylamine hydrochloride and tetradecyldi(aminoethyl)glycine.

$$C_{16}H_{33}-N^+H(CH_3)_2 \cdot Cl^- \quad (XI)$$

$$C_{14}H_{29}NHCH_2CH_2NHCH_2CH_2N^+H_2CH_2COO^- \quad (XII)$$

One example of an organic compound with a quaternary nitrogen is tetraalkyl ammonium. It is also acceptable for the compound to have a hydrocarbon group that contains another element such as an imino group, ether group, etc., or for the compound to have an allyl group instead of an alkyl group. As a preferred example, there is the dodecyltrimethylammonium chloride shown in formula XIII.

$$C_{12}H_{25}N^+(CH_3)_3 \cdot Cl^- \quad (XIII)$$

In addition to these chemical compounds with a relatively low molecular weight, it is also possible to use organic polymers that have a quaternary nitrogen. As such a polymer, the polycation shown by the general formula XIV with a repeating unit can be mentioned.

(wherein $R_9-R_{12}$ is hydrogen or an alkyl group, X is a halogen group or acid moiety, and Y is an alkylene group or alkylene group-$SO_2-$, and the above-mentioned unit is repeated 5-2000 times.)

Of the compounds of formula XIV, polycations with repeated units such as those shown in formula XV and XVI are particularly suitable.

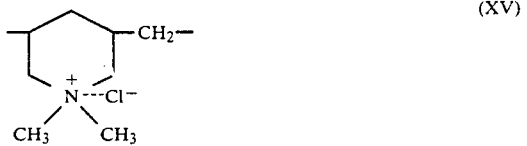

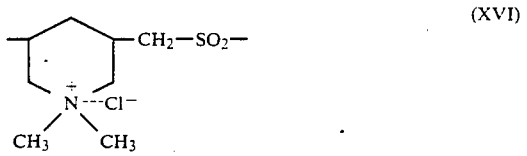

When the heparin-neutralizing agent mentioned above is included, the proportions are 5-10,000 parts by weight of the said neutralizing agent to 100 parts by weight of the metal complex. If there is not enough of the neutralizing agent, then when the blood contains heparin, the heparin will not be neutralized and so the blood will not coagulate. If there is too much of the neutralizing agent, the effects compared with those obtained with the proportions mentioned above are not achieved.

In the accelerator of blood coagulation of this invention, an anti-fibrinolysis agent and/or an antiplasmin agent can be included. Aprotinin, soybean trypsin inhibitor, ε-aminocaproic acid, p-aminomethylbenzoic acid, 4-(aminomethyl)cyclohexanecarboxylic acid, etc., which are conventionally used clinically, can be used as the anti-fibrinolysis agent and/or the anti-plasmin agent. These can be used independently or in combination. For example, aprotinin is used at the proportion of about 100–600 KIU per milliliter of blood, soybean trypsin inhibitor is used at the proportion of about 500–4000 FU per milliliter of blood, and ε-aminocaproic acid, p-aminomethylbenzoic acid, and 4-(aminomethyl)-cyclohexanecarboxylic acid are all used at the proportion of about $10^{-2}-10^{-8}$ g per milliliter of blood in the accelerator of blood coagulation.

The accelerator of blood coagulation of this invention is used at proportions in the range of $1 \times 10^{-10}$ to $1 \times 10^{-1}$ g per milliliter of blood. If the proportion is too small, the effects of acceleration of blood coagulation will not be obtained. If there is an excess, results will not be attained with the proportion to the amount used.

When the accelerator of blood coagulation of this invention is used, the vessels to contain the blood for testing can be of either glass or resin. It is acceptable for the accelerator of blood coagulation to be added to the blood after it has been collected into the vessel, and it is also acceptable for the accelerator of blood coagulation to be present already in the vessel to be used before blood sampling. The accelerator of blood coagulation can be in the form of a powder, and it can also be dissolved, in advance, in an appropriate solvent. When the accelerator of blood coagulation is used in the form of a powder, or as a solution of high concentration, and when one portion of the blood may come into contact with the blood coagulation accelerator at a high concentration, so that there is the danger that the protein of the blood may be denatured, the said accelerator of blood coagulation should be held on a carrier that has a specific surface area that is large.

For the carrier that is used in this way, there are no special restrictions, provided that there is no harmful effect on the blood test results and that the carrier has a large specific surface area. For example, unwoven cloth, textiles, resin beads, etc., are suitable for use. To hold the accelerator of blood coagulation on such a carrier, for example, the solution or dispersion of the accelerator can be applied to the carrier, or the carrier can be immersed in a solution or dispersion of the accelerator, after which it is dried. Water that contains appropriate assistant agents such as gum arabic, etc., is prepared and used for a dispersion of the accelerator of blood coagulation, and this can be lyophilized, resulting in a accelerator of blood coagulation held on a carrier in particulate form.

The accelerator of the activity of hydrolase of this invention is an accelerator of the activity of enzymes that decompose proteins, and especially an accelerator of serine protease. Serine protease has the ability to cut, by hydrolysis, the bond of peptide chains between Arg and any amino acid residue and also the bond between Lys and any amino acid residue. The accelerator of the activity of hydrolase of this invention, when used as an accelerator of blood coagulation, first activates Factor XII, which is one kind of precursor of serine protease.

Then, the enzyme reaction of the activated Factor XII is further accelerated, and the other blood coagulation factors in the blood are activated in turn, so that the blood coagulates in a short period of time. When in the accelerator of blood coagulation, serine protease and/or other such enzymes that hydrolyze protein are present as a co-accelerator, the activation of the coagulation factors in the blood is further accelerated. It is thought that the accelerator of the activity of hydrolase contained in the accelerator of blood coagulation accelerates the reaction of these enzymes that hydrolyze proteins. As a result, the blood coagulates in a short period of time.

When an organic compound that has an amine salt or a quaternary nitrogen is contained in the accelerator of blood coagulation, this accelerator of blood coagulation can be used to coagulate blood that contains heparin. If such an accelerator of blood is added to blood that contains heparin, the neutralizer of the amine salt, etc., adsorbs, neutralizes, and precipitates the heparin, so that the inhibition of thrombin and Factor XII by the heparin can be eliminated. For that reason, the normal ability of the blood to coagulate is restored. In addition, a hydrolase activity accelerator (metal complex) contained in the accelerator of blood coagulation has the ability to act on the Factor XII in the blood to activate it. So, as when normal blood is treated, the blood coagulates rapidly.

When an anti-fibrinolysis agent and/or an anti-plasmin agent is also included in addition to the above-mentioned amino salts, etc., the decomposition of fibrin by plasmin, which competes with the coagulation reaction of the blood, is inhibited. For that reason, the coagulation of the blood is accelerated, and in addition, after coagulation, the coagulation is stable.

Depending on the metal complex and the variety of neutralizer contained in the accelerator of blood coagulation, the amount of accelerator of blood coagulation, the material of the vessel used, the amount of heparin in the blood, and the like, the time needed for blood coagulation varies. When the metal complex is the sole main ingredient, and if a vessel made of synthetic resin is used, the time needed is generally about 20-30 minutes; when a hydrolase is included as a co-accelerator, it takes about 3-7 minutes under the same conditions. When blood that contains heparin is treated, it takes about 20-40 minutes for coagulation under the same conditions.

As mentioned above, it is possible by use of the accelerator of blood coagulation of this invention to coagulate blood that is normal and also blood that contains heparin in a short period of time. The blood clot satisfactorily aggregates, and the separation effect of the serum and the blood clot is excellent. So, when the serum is obtained, the blood clot does not mix with the serum, and it is possible to obtain serum in a high yield.

The compound that is the main ingredient of the accelerator of blood coagulation of this invention is a metal complex, so compared to the organic cyclic compound I included in the accelerator of blood coagulation already disclosed by the inventors, the stability to heat is still greater. Accordingly, even when the accelerator of blood coagulation of this invention undergoes such treatment as autoclave sterilization, etc., the function thereof is not reduced. It is also possible to store this accelerator satisfactorily for long periods of time. When the above-mentioned organic cyclic compound is used as the accelerator of blood coagulation, there is the danger that changes the some kinds of serum components, but the compound included in the accelerator of blood coagulation of this invention does not react with the components in the blood, so that accurate test results can be obtained.

EXAMPLE 1-1

First, 50 μl of physiological saline dispersion liquid containing oxidized n-propyl gallate-iron complex (accelerator of blood coagulation) in a concentration of 0.1% by weight was put into a commercially available tube made of polymethylmethacrylate, and then 5 ml of freshly collected human blood was added, and the tube was left at 23° C. The time at which the blood clot was seen to begin to form and at which serum appeared was taken to be the blood coagulation time. As soon as serum appeared, the sample was put into a centrifuge and centrifuged at 1000 ×g for 5 minutes. The separation effect of the serum was observed by eye. The results obtained are given in Table 1. Results from Examples 1-2 to 1-8 and Comparative Examples 1-1 and 1-2 are given in Table 1 as well.

EXAMPLE 1-2

An iron complex of oxidized ellagic acid (a compound with the structure shown in formula V) as the accelerator of blood coagulation was used. Other conditions were the same as those given for Example 1-1.

EXAMPLE 1-3

An iron complex of 1,2,3-triketohydroindene as the accelerator of blood coagulation was used. Other conditions were the same as those given for Example 1-1.

EXAMPLE 1-4

An iron complex of isatin as the accelerator of blood coagulation was used. Other conditions were the same as those given for Example 1-1.

EXAMPLE 1-5

An iron complex of oxidized 1,4-di(3,4-dihydroxyphenyl) 2,3-dimethylbutane as the accelerator of blood coagulation was used. Other conditions were the same as those given for Example 1-1.

EXAMPLE 1-6

A cobalt complex was used instead of an iron complex. Other conditions were the same as those given for Example 1-2.

EXAMPLE 1-7

A nickel complex was used instead of an iron complex. Other conditions were the same as those given for Example 1-2.

EXAMPLE 1-8

An aluminum complex was used instead of an iron complex. Other conditions were the same as those given for Example 1-2.

COMPARATIVE EXAMPLE 1-1

The accelerator of blood coagulation was not used. Other conditions were the same as those given for Example 1-1.

COMPARATIVE EXAMPLE 1-2

A tube made of glass was used, and the accelerator of blood coagulation was not used. Other conditions were the same as those given for Example 1-1.

EXAMPLE 2 (2-1)

An iron complex of 1,2,3-triketohydroindene as a metallic complex was used. Other conditions were the same as those given for Example 2 (1-1).

TABLE 1

|  | Accelerator of the activity of hydrolase | Blood coagulation time (minute) | Separation effect of the serum | Spitz |
|---|---|---|---|---|
| Example 1-1 | Oxidized n-propyl gallate-iron complex | 30 | Excellent | Polymethyl methacrylate |
| Example 1-2 | Oxidized ellagic acid-iron complex | 25 | Excellent | Polymethyl methacrylate |
| Example 1-3 | 1.2.3-triketohydroindene-iron complex | 30 | Excellent | Polymethyl methacrylate |
| Example 1-4 | Isatin-iron complex | 25 | Excellent | Polymethyl methacrylate |
| Example 1-5 | Oxidized 1.4-di(3.4-dihydroxyphenyl) 2.3-dimethylbutane-iron complex | 30 | Excellent | Polymethyl methacrylate |
| Example 1-6 | Oxidized ellagic acid-coball complex | 25 | Excellent | Polymethyl methacrylate |
| Example 1-7 | Oxidized ellagic acid-nickel complex | 25 | Excellent | Polymethyl methacrylate |
| Example 1-8 | Oxidized ellagic acid aluminum complex | 25 | Excellent | Polymethyl methacrylate |
| Comparative Example 1-1 | — | 260 | Precipitate of fibrin in the serum | Polymethyl methacrylate |
| Comparative Example 1-2 | — | 65 | Precipitate of fibrin in the serum | Glass |

EXAMPLE 2 (1-1)

A physiological saline solution dispersion liquid, which contained an iron complex of oxidized ellagic acid (a compound with the structure shown in formula V) as an agent to activate blood coagulation factors (the metal complex), and trypsin as a co-accelerator of blood coagulation in concentrations of 0.5% by weight and 0.05% by weight, respectively, was prepared. Freshly collected human blood (3 ml) was put into a commercially available plain tube made of polyethylene, and 30 $\mu$l of the solution of the accelerator of blood coagulation described above was added thereto. The plain tube was left at room temperature, and the time needed for the blood to lose its ability to flow was measured, and taken to be the blood coagulation time. Then, the sample was centrifuged after coagulation at 3000 rpm for 5 minutes, and the separation effect of the serum was evaluated by eye. The results are shown in Table 2. Results for Examples 2 (1-2) to 2 (4-3) are also given in Table 2.

EXAMPLE 2 (1-2)

Thrombin was used as a hydrolase of a co-accelerator, and a physiological saline solution dispersion liquid of the accelerator of blood coagulation was prepared so that the concentration of the said enzyme was 500 units/ml. Other conditions were the same as in Example 2 (1-1).

EXAMPLE 2 (1-3)

Snake venom thrombin-like enzyme was used as a hydrolase of a co-accelerator, and a physiological saline solution dispersion liquid of the accelerator of blood coagulation was prepared so that the concentration of the said enzyme was 0.005% by weight. Other conditions were the same as in Example 2 (1-1).

EXAMPLE 2 (2-2)

An iron complex of 1,2,3-triketohydroindene as a metallic complex was used. Other conditions were the same as those given for Example 2 (1-2).

EXAMPLE 2 (2-3)

An iron complex of 1,2,3-triketohydroindene as a metallic complex was used. Other conditions were the same as those given for Example 2 (1-3).

EXAMPLE 2 (3-1)

An iron complex of oxidized n-propyl gallate as a metallic complex was used. Other conditions were the same as those given for Example 2 (1-1).

EXAMPLE 2 (3-2)

An iron complex of oxidized n-propyl gallate as a metallic complex was used. Other conditions were the same as those given for Example 2 (1-2).

EXAMPLE 2 (3-3)

An iron complex of oxidized n-propyl gallate as a metallic complex was used. Other conditions were the same as those given for Example 2 (1-3).

EXAMPLE 2 (4-1)

An iron complex of isatin as a metallic complex was used. Other conditions were the same as those given for Example 2 (1-1).

EXAMPLE 2 (4-2)

An iron complex of isatin as a metallic complex was used. Other conditions were the same as those given for Example 2 (1-2).

EXAMPLE 2 (4-3)

An iron complex of isatin as a metallic complex was used. Other conditions were the same as those given for Example 2 (1-3).

EXAMPLE 2 (5-1)

A cobalt complex of oxidized ellagic acid (a compound with the structure shown in formula V) as a metallic complex was used. Other conditions were the same as those given for Example 2 (1-1). The results obtained are given in Table 3. Results from Examples 2 (5-2) to 2 (7-3) are given in Table 3 as well.

EXAMPLE 2 (5-2)

A cobalt complex of oxidized ellagic acid (a compound with the structure shown in formula V) as a metallic complex was used. Other conditions were the same as those given for Example 2 (1-2).

EXAMPLE 2 (5-3)

A cobalt complex of oxidized ellagic acid (a compound with the structure shown in formula V) as a metallic complex was used. Other conditions were the same as those given for Example 2 (1-3).

EXAMPLE 2 (6-1)

A nickel complex of oxidized ellagic acid (a compound with the structure shown in formula V) as a metallic complex was used. Other conditions were the same as those given for Example 2 (1-1).

EXAMPLE 2 (6-2)

A nickel complex of oxidized ellagic acid (a compound with the structure shown in formula V) as a metallic complex was used. Other conditions were the same as those given for Example 2 (1-2).

EXAMPLE 2 (6-3)

A nickel complex of oxidized ellagic acid (a compound with the structure shown in formula V) as a metallic complex was used. Other conditions were the same as those given for Example 2 (1-3).

EXAMPLE 2 (7-1)

An aluminum complex of oxidized ellagic acid (a compound with the structure shown in formula V) as a metallic complex was used. Other conditions were the same as those given for Example 2 (1-1).

EXAMPLE 2 (7-2)

An aluminum complex of oxidized ellagic acid (a compound with the structure shown in formula V) as a metallic complex was used. Other conditions were the same as those given for Example 2 (1-2).

EXAMPLE 2 (7-3)

An aluminum complex of oxidized ellagic acid (a compound with the structure shown in formula V) as a metallic complex was used. Other conditions were the same as those given for Example 2 (1-3).

Comparative Example 2-1

Trypsin was used alone as the accelerator of blood coagulation. Other conditions were the same as given for Example 2 (1-1).

COMPARATIVE EXAMPLE 2-2

Thrombin was used alone as the accelerator of blood coagulation. Other conditions were the same as given for Example 2 (1-2).

COMPARATIVE EXAMPLE 2-3

Snake venom thrombin-like enzymes were used alone as the accelerator of blood coagulation. Other conditions were the same as given for Example 2 (1-3).

COMPARATIVE EXAMPLE 2-4

The accelerator of blood coagulation was not used. Other conditions were the same as those given for Example 2 (1-1).

COMPARATIVE EXAMPLE 2-5

The accelerator of blood coagulation was not used, and a glass Spitz was used. Other conditions were the same as those given for Example 2 (1-1).

TABLE 2

|  | Metallic complex | Hydrolase | Blood coagulation time (minute) | Separation effect of the serum | Spitz |
|---|---|---|---|---|---|
| Example 2 (1-1) | Oxidized ellagic acid(V)-iron complex | Trypsin | 5 | Excellent | Polyethylene |
| Example 2 (1-2) | Oxidized ellagic acid(V)-iron complex | Thrombin | 3 | Excellent | Polyethylene |
| Example 2 (1-3) | Oxidized ellagic acid(V)-iron complex | Snake venom thrombin-like enzymes | 5 | Excellent | Polyethylene |
| Example 2 (2-1) | 1.2.3-triketohydroindene-iron complex | Trypsin | 5 | Excellent | Polyethylene |
| Example 2 (2-2) | 1.2.3-triketohydroindene-iron complex | Thrombin | 4 | Excellent | Polyethylene |
| Example 2 (2-3) | 1.2.3-triketohydroindene-iron complex | Snake venom thrombin-like enzymes | 4 | Excellent | Polyethylene |
| Example 2 (3-1) | Oxidized n-propyl gallate-iron complex | Trypsin | 6 | Excellent | Polyethylene |
| Example 2 (3-2) | Oxidized n-propyl gallate-iron complex | Thrombin | 4 | Excellent | Polyethylene |
| Example 2 (3-3) | Oxidized n-propyl gallate-iron complex | Snake venom thrombin-like enzymes | 5 | Excellent | Polyethylene |
| Example 2 (4-1) | Isatin-iron complex | Trypsin | 7 | Excellent | Polyethylene |
| Example 2 (4-2) | Isatin-iron complex | Thrombin | 3 | Excellent | Polyethylene |
| Example 2 (4-3) | Isatin-iron complex | Snake venom thrombin-like enzymes | 5 | Excellent | Polyethylene |

TABLE 3

| | Metallic complex | Hydrolase | Blood coagulation time (minute) | Separation effect of the serum | Spitz |
|---|---|---|---|---|---|
| Example 2 (5-1) | Oxidized ellagic acid(V)-cobalt complex | Trypsin | 5 | Excellent | Polyethylene |
| Example 2 (5-2) | Oxidized ellagic acid(V)-cobalt complex | Thrombin | 4 | Excellent | Polyethylene |
| Example 2 (5-3) | Oxidized ellagic acid(V)-cobalt complex | Snake venom thrombin-like enzymes | 5 | Excellent | Polyethylene |
| Example 2 (6-1) | Oxidized ellagic acid(V)-nickel complex | Trypsin | 5 | Excellent | Polyethylene |
| Example 2 (6-2) | Oxidized ellagic acid(V)-nickel complex | Thrombin | 5 | Excellent | Polyethylene |
| Example 2 (6-3) | Oxidized ellagic acid(V)-nickel complex | Snake venom thrombin-like enzymes | 4 | Excellent | Polyethylene |
| Example 2 (7-1) | Oxidized ellagic acid(V)-aluminum complex | Trypsin | 5 | Excellent | Polyethylene |
| Example 2 (7-2) | Oxidized ellagic acid(V)-aluminum complex | Thrombin | 4 | Excellent | Polyethylene |
| Example 2 (7-3) | Oxidized ellagic acid(V)-aluminum complex | Snake venom thrombin-like enzymes | 5 | Excellent | Polyethylene |

TABLE 4

| | Metallic complex | Hydrolase | Blood coagulation time (minute) | Separation effect of the serum | Spitz |
|---|---|---|---|---|---|
| Comparative Example 2-1 | — | Trypsin | 14 | Excellent | Polyethylene |
| Comparative Example 2-2 | — | Thrombin | 14 | Excellent | Polyethylene |
| Comparative Example 2-3 | — | Snake venom thrombin-like enzymes | 40 | Free blood cells seen | Polyethylene |
| Comparative Example 2-4 | — | — | 330 | Supernatant contained fibrin | Polyethylene |
| Comparative Example 2-5 | — | — | 60 | Supernatant contained much fibrin | Glass |

EXAMPLE 3-1

First, an aqueous dispersion liquid containing an iron complex of oxidized ellagic acid (a compound with the structure of formula V) and polycation (a compound with the structure of formula XVI) was prepared. A non-woven cloth of polyacetate was then impregnated with the dispersion, and dried thoroughly. There was $10^{-4}$ g of each of the above two components contained on each square centimeter of unwoven cloth.

Then, 8 ml of freshly collected human blood that contained heparin at the concentration of 2 units/ml was injected into a commercially available 10-ml tube made of polyethylene, and 1 cm$^2$ of the unwoven cloth carrying the above-mentioned ingredients thereon was added and gently agitated before being left at 20° C. The time needed for the whole blood to lose its ability to flow was taken to be the blood coagulation time.

As soon as the blood had coagulated, it was centrifuged for 5 minutes at the rate of 3000 rpm. Then the separation effect of the serum was evaluated by eye. The serum was obtained by the use of a pipette, and its volume was taken to be the yield of serum. These results are shown in Table 5. Results of Examples 3-2 to 3-10 and of Comparative Example 3 are also given in Table 5.

EXAMPLE 3-2

A physiological saline solution dispersion liquid containing oxidized n-propyl gallate-iron complex and tetradecyldi(aminoethyl)glycine in concentrations of 0.5% and 0.2% by weight, respectively, was prepared.

In a 10-ml commercially available tube made of polyethylene, 8 ml of freshly collected human blood that contained 2 units of heparin per milliliter was injected, and then 80 μl of the above-mentioned dispersion liquid was added thereto. Other treatment was the same as in Example 3-1, and the results were evaluated.

EXAMPLE 3-3

First, 1 g of the iron complex isatin, 0.4 g of hexadecyldimethylamine hydrochloride, and 1 kg of polystyrene beads with the mean diameter of 1.5 mm. as a carrier were mixed well with a small volume of ethanol as the assistant agent for dispersal. The mixture was then dried. In one gram of the said particulate holding thereon the accelerator of blood coagulation, there was $10^{-3}$ g of iron complex of isatin and $0.4 \times 10^{-3}$ g of hexadecyldimethylamine hydrochloride.

In a 10-ml commercially available tube made of polyethylene, 8 ml of freshly collected human blood that contained 2 units of heparin per milliliter was injected, and then 1 g of the above-mentioned particulate holding thereon the accelerator of blood coagulation was added thereto. The sample was treated as for Example 3-1, and then evaluated.

EXAMPLE 3-4

An iron complex of o-quinone and polycation (a compound with the structure shown in formula XV) were used instead of the iron complex of oxidized n-propyl gallate and tetradecyldi(aminoethyl)glycine, respectively. The iron complex of o-quinone and polycation were employed in concentration of 0.5% by weight and 0.4% by weight, respectively. Other conditions were the same as those given for Example 3-2.

EXAMPLE 3-5

An iron complex of 1,2,3-triketohydroindene and polycation (a compound with the structure shown in formula XVI) were used instead of the iron complex of oxidized n-propyl gallate and tetradecyldi(aminoethyl)glycine, respectively. Other conditions were the same as those given for Example 3-2.

EXAMPLE 3-6

Dodecyltrimethylammonium chloride were used instead of the tetradecyldi(aminoethyl)glycine. Other conditions were the same as those given for Example 3-2.

EXAMPLE 3-7

An iron complex of oxidized 1,4-di(3,4-dihydroxyphenyl)2,3-dimethylbutane and polycation (and polycation (a compound with the structure shown in formula XV) were used instead of the iron complex of oxidized n-propyl gallate and tetradecyldi(aminoethyl)glycine. Other conditions were the same as those given for Example 3-2.

EXAMPLE 3-8

A cobalt complex of oxidized ellagic acid (V) and polycation (a compound with the structure shown in formula XV) were used instead of the iron complex of oxidized n-propyl gallate and tetradecyldi(aminoethyl)glycine. Other conditions were the same as those given for Example 3-2.

EXAMPLE 3-9

A nickel complex of ellagic acid (V) and polycation (a compound with the structure shown in formula XV) were used instead of the iron complex of oxidized n-propyl gallate and tetradecyldi(aminoethyl)glycine. Other conditions were the same as those given for Example 3-2.

EXAMPLE 3-10

An aluminum complex of ellagic acid (V) and polycation (a compound with the structure shown in formula XV) were used instead of the iron complex of oxidized n-propyl gallate and tetradecyldi(aminoethyl)glycine. Other conditions were the same as those given for Example 3-2.

COMPARATIVE EXAMPLE 3

In a 10-ml commercially available tube made of polyethylene, 8 ml of freshly collected human blood that contained 2 units of heparin per milliliter was injected, and then without the addition of the accelerator of blood coagulation, the same treatment as for Example 3-1 was carried out, and the results were evaluated.

TABLE 5

| | Accelerator of the activity of hydrolase | | Blood coagulation | Separation effect of | Yield of serum |
|---|---|---|---|---|---|
| | Metallic complex | Neutralizing-agent | time (minute) | the serum | (ml) |
| Example 3-1 | Oxidized ellagic acid (V)-iron complex | Polycation (XVI) | 35 | Excellent | 4.0 |
| Example 3-2 | Oxidized n-propyl gallate-iron complex | Tetradocyldi(aminoethyl)glycine | 35 | Excellent | 4.1 |
| Example 3-3 | Isatin-iron complex | Hexadecyldimethylamine hydrochloide | 35 | Excellent | 4.1 |
| Example 3-4 | o-quinone-iron complex | Polycation (XV) | 35 | Excellent | 4.0 |
| Example 3-5 | 1,2,3-triketohydroindene-iron complex | Polycation (XVI) | 40 | Excellent | 4.1 |
| Example 3-6 | Oxidized n-propyl gallate-iron complex | Dodecyltrimethylammonium chloride | 35 | Excellent | 4.1 |
| Example 3-7 | Oxidized 1,4-di(3,4-dihydroxylphenyl(2,3-dimethylbutane-iron complex | Polycation (XV) | 40 | Excellent | 4.1 |
| Example 3-8 | Oxidized ellagic acid (V)-cobalt complex | Polycation (XV) | 35 | Excellent | 4.1 |
| Example 3-9 | Oxidized ellagic acid (V)-nickel complex | Polycation (XV) | 35 | Excellent | 4.0 |
| Example 3-10 | Oxidized ellagic acid (V)-aluminum complex | Polycation (XV) | 40 | Excellent | 4.0 |
| Comparative Example 3 | — | — | Not coagulated | Separation of the plasma | — |

EXAMPLE 4-1

Polyester unwoven cloth was impregnated with an aqueous dispersion liquid containing an iron complex of oxidized ellagic acid (a compound with the structure shown in formula V), polycation (a compound with the structure shown in formula XVI), and aprotinin, and was then completely dried. There were, per square centimeter of unwoven cloth, $4 \times 10^{-4}$ g of the iron complex, $4 \times 10^{-4}$ g of polycation, and 500 KIU of aprotinin.

In a 5-ml commercially available tube made of polyethylene, 2 ml of freshly collected human blood that contained 1.0 IU of heparin per milliliter was injected, and then 1 cm² of the unwoven cloth holding thereon the ingredients mentioned above was added thereto, gently agitated, and then left at 20° C. One hour later, or 30 hours later, the serum was collected, and the fibrin and fibrinogen degradation product (FDP) were assayed. The results are given in Table 6. There was no difference in the results of assays of FDP after 1 hour or 30 hours, which shows that the decomposition reaction of the blood clot was inhibited. Results for Examples 4-2 to 4-10 and of Comparative Example 4 are also given in Table 6.

EXAMPLE 4-2

A dispersion in physiological saline solution was made so that the concentration of oxidized n-propyl gallate was 0.5 % by weight, that of tetradecyldi(aminoethyl)glycine was 0.5% by weight, and that of aprotinin was 10,000 KIU/ml.

In a 5-ml commercially available tube made of polyethylene, 2 ml of freshly collected human blood that contained 1.0 IU of heparin was injected, and then 50 μl of the dispersion liquid mentioned above was added thereto. Then, the sample was treated as in Example 4-1, and the results were evaluated.

EXAMPLE 4-3

First, 1 g of isatin, 0.4 g of hexadecyldimethylamine hydrochloride, 50 mg of 4-(aminomethyl)cyclohexanecarboxylic acid, and 1 kg of polystyrene beads with the mean diameter of 1.5 mm as a carrier were mixed thoroughly with a small amount of ethanol as assistant agent for dispersal, and dried.

In a 5-ml commercially available tube made of polyethylene, 2 ml of freshly collected human blood that contained 1.0 IU of heparin per milliliter was injected. Then, 0.3 g of the accelerator of blood coagulation described above was added thereto. Then, the sample was treated as in Example 4-1, and the results were evaluated.

EXAMPLE 4-4

An iron complex of o-quinone, a polycation (a compound with the structure shown in formula XV) and ε-aminocaproic acid were used instead of the iron complex of oxidized n-propyl gallate, tetradecyl(aminoethyl)glycine and aprotinin. The iron complex of o-quinone, the polycation and the ε-aminocaproic acid were employed in concentrations of 0.5% by weight, 0.5% by weight and 0.1% by weight, respectively. Other conditions were the same as those given for Example 4-2.

EXAMPLE 4-5

An iron complex of 1,2,3-triketohydroindene, a polycation (a compound with the structure shown in formula XVI) and ε-aminocaproic acid were used instead of the iron complex of oxidized n-propyl gallate, tetradecyl(aminoethyl)glycine and aprotinin. Other conditions were the same as those given for Example 4-2.

EXAMPLE 4-6

Dodecyltrimethylammonium chloride was used instead of the tetradecyldi(aminoethyl)glycine. Other conditions were the same as those given for Example 4-2.

EXAMPLE 4-7

An oxidized iron complex of 1,4-di(3,4-dihydroxyphenyl) 2,3-dimethylbutane and polycation (a compound with the structure shown in formula XV) were used instead of the iron complex of oxidized n-propyl gallate and tetradecyldi(aminoethyl)glycine. Other conditions were the same as those given for Example 4-2.

EXAMPLE 4-8

A cobalt complex of oxidized ellagic acid (V) and polycation (a compound with the structure shown in formula XV) were used instead of the iron complex of oxidized n-propyl gallate and tetradecyldi(aminoethyl)glycine. Other conditions were the same as those given for Example 4-2.

EXAMPLE 4-9

A nickel complex of oxidized ellagic acid (V) and polycation (a compound with the structure shown in formula XV) were used instead of the iron complex of oxidized n-propyl gallate and tetradecyldi(aminoethyl)glycine. Other conditions were the same as those given for Example 4-2.

EXAMPLE 4-10

An aluminium complex of oxidized ellagic acid (V) and polycation (a compound with the structure shown in formula XV) were used instead of the iron complex of oxidized n-propyl gallate and tetradecyldi(aminoethyl)glycine. Other conditions were the same as those given for Example 4-2.

TABLE 6

| | Accelerator of the activity of hydrolase | | | Results of assays of FDP | |
|---|---|---|---|---|---|
| | Metallic complex | Neutralizing-agent | Anti-fibrinolysis agent | After one hour | After thirty hours |
| Example 4-1 | Oxidized ellagic acid (V)-iron complex | Polycation (XVI) | Aprotinin | 2.5 μg/ml or less | 2.5 μg/ml or less |
| Example 4-2 | Oxidized n-propyl gallate-iron complex | Tetradocyldi(aminoethyl) glycine | Aprotinin | 2.5 μg/ml or less | 2.5 μg/ml or less |
| Example 4-3 | Isatin-iron complex | Hexadecyldimethylamine hydrochloide | Aminomethylcyclohexane carboxylic acid | 2.5 μg/ml or less | 2.5 μg/ml or less |
| Example 4-4 | o-quinone-iron complex | Polycation (XV) | ε-aminocaproic acid | 2.5 μg/ml or less | 2.5 μg/ml or less |
| Example 4-5 | 1,2,3-triketohydroindene-iron complex | Polycation (XVI) | ε-aminocaproic acid | 2.5 μg/ml or less | 2.5 μg/ml or less |
| Example 4-6 | Oxidized n-propyl gallate-iron complex | Dodecyltrimethylammonium chloride | Aprotinin | 2.5 μg/ml or less | 2.5 μg/ml or less |
| Example 4-7 | Oxidized 1,4-di(3,4-dihydroxylphenyl(2,3-dimethylbutane-iron complex | Polycation (XV) | Aprotinin | 2.5 μg/ml or less | 2.5 μg/ml or less |
| Example 4-8 | Oxidized ellagic acid (V)-cobalt complex | Polycation (XV) | Aprotinin | 2.5 μg/ml or less | 2.5 μg/ml or less |
| Example 4-9 | Oxidized ellagic acid (V)-nickel complex | Polycation (XV) | Aprotinin | 2.5 μg/ml or less | 2.5 μg/ml or less |
| Example 4-10 | Oxidized ellagic acid (V)-aluminum complex | Polycation (XV) | Aprotinin | 2.5 μg/ml or less | 2.5 μg/ml or less |

EXAMPLE 4-11

All of the accelerators of blood coagulation described in Examples 4-1 to 4-10 were prepared. Each accelerator was placed into a tube for blood collection, and then freshly collected human blood that contained heparin was injected into the tube. The tubes were gently agitated, and left at 20° C. Then the samples were timed for the time needed for the whole blood to lose its ability to flow. That is, the blood coagulation time was measured. In all of the examples, blood coagulated in 35-40 minutes. After the blood had coagulated, the samples were immediately centrifuged at the speed of 3000 rpm for 5 minutes, and the separation effect of the serum was evaluated by eye. The collection of the serum by pipette was also studied. In all examples, the separation effect of serum and the yield of serum were excellent.

EXAMPLE 5-1

First, 50 -1 of physiological saline solution dispersion liquid containing an iron complex of oxidized ellagic acid (a compound with the structure shown in formula V) in a concentration of 0.1% by weight was put into a commercially available tube made of polymethylmethacrylate, and then 5 ml of freshly collected human blood was added thereto, and the tube was left at 23 ° C. After the completion of blood coagulation, the sample was centrifuged at 1000×g for 5 minutes so as to separate the serum from the blood clot. Then, uric acid (UA), phospholipids (PL) and triglycerides (TG) that are present in the separated serum were measured, the results of which are shown in Table 7. The results from Comparative Examples 5-1 and 5-2 mentioned below are shown in Table 7 as well.

Comparative Example 5-1

This example is the same as Example 5-1 except that oxidized ellagic acid shown in formula V was used as an accelerator of blood coagulation.

COMPARATIVE EXAMPLE 5-2

This example is the same as Example 5-1 except that the dispersion liquid of the accelerator of blood coagulation was not used.

According to the comparison with Comparative Example 5-2, Table 7 indicates that UA, PL, and TG can be measured with accuracy in the serum obtained from Example 5-1 in which metal complex was used as an accelerator of blood coagulation, whereas the contents of UA, PL, and TG in the serum obtained from Comparative Example 5-1 in which oxidized ellagic acid that does not form a metal complex was used cannot be accurately measured (namely, the contents of UA, PL, and TG in the serum of this comparative example are lower than those of UA, PL, and TG in the serum from Comparative Example 5-2). These facts mean that the accelerator of blood coagulation of Comparative EXAMPLE 5-1 influences the assay of the contents of the above-mentioned components in the serum for the worse.

TABLE 7

|  | UA (mg/dl) | PL (mg/dl) | TG (mg/dl) |
| --- | --- | --- | --- |
| Example 5-1 | 6.1 | 155 | 90 |
| Comparative Example 5-1 | 5.0 | 130 | 64 |
| Comparative Example 5-2 | 6.1 | 156 | 93 |

EXAMPLE 6

First, 5 ml of an aqueous dispersion liquid containing an iron complex (an accelerator of blood coagulation) of oxidized ellagic acid (a compound represented by formula V) in a concentration of 0.1% by weight was put into a hard glass tube, which was then heat-treated at 121° C. for 1 hour under two atmospheres of pressure. The said accelerator of blood coagulation was not denatured at all before and after such autoclave treatment.

COMPARATIVE EXAMPLE 6

First, 5 ml of an aqueous dispersion liquid containing oxidized ellagic acid (a compound represented by formula V) in a concentration of 0.1% by weight was put into a hard glass tube, which was then autoclaved in the same manner as that of Example 6. The oxidized ellagic acid, which was blackish-brown before the said autoclave treatment, became yellowish-white after the autoclave treatment. Moreover, the oxide became water-soluble, which means that the oxide was denatured.

It is understood that various other modifications will be apparent to and can be readily made by those skilled in the art without departing from the scope and spirit of this invention. Accordingly, it is not intended that the scope of the claims appended hereto be limited to the description as set forth herein, but rather that the claims be construed as encompassing all the features of patentable novelty that reside in the present invention, including all features that would be treated as equivalents thereof by those skilled in the art to which this invention pertains.

What is claimed is:

1. An accelerator of the activity of hydrolase, comprising an iron complex containing the oxidized ellagic acid of Structure V as a ligand.

(I)

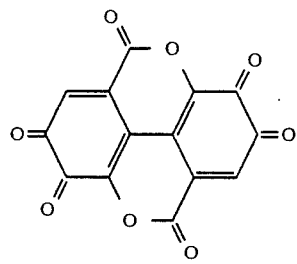

(V)

2. An accelerator according to claim 1, wherein said hydrolase is serine protease.

3. An accelerator according to claim 2, wherein said serine protease is blood coagulation Factor XII.

4. The accelerator of claim 1, wherein said iron complex accelerates blood coagulation.

5. The accelerator of claim 2, wherein said iron complex accelerates blood coagulation.

6. The accelerator of claim 3, wherein said iron complex accelerates blood coagulation.

* * * * *

UNITED STATES PATENT AND TRADEMARK OFFICE
CERTIFICATE OF CORRECTION

PATENT NO. : 5,041,558
DATED : August 20, 1991
INVENTOR(S) : Hideo Anraku It is certified that error appears in the above-identified patent and that said Letters Patent is hereby corrected as shown below:

In column 22, line 40
The formula and reference

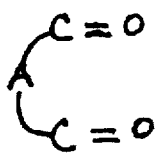

should be deleted.

Signed and Sealed this

Ninth Day of March, 1993

*Attest:*

STEPHEN G. KUNIN

*Attesting Officer*     *Acting Commissioner of Patents and Trademarks*